United States Patent
Fischer

(10) Patent No.: US 9,622,797 B2
(45) Date of Patent: Apr. 18, 2017

(54) DETECTION AND DISPLAY DEVICE FOR PEDICLE SCREW AND SPINAL STABILIZATION SYSTEM WITH DETECTION AND DISPLAY DEVICE

(71) Applicant: Aesculap AG, Tuttlingen (DE)

(72) Inventor: Kay Fischer, Tuttlingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 15/014,375

(22) Filed: Feb. 3, 2016

(65) Prior Publication Data

US 2016/0228159 A1    Aug. 11, 2016

(30) Foreign Application Priority Data

Feb. 5, 2015  (DE) .......................... 10 2015 101 650

(51) Int. Cl.
*A61B 17/70*   (2006.01)
(52) U.S. Cl.
CPC ...... *A61B 17/7083* (2013.01); *A61B 17/7074* (2013.01)
(58) Field of Classification Search
CPC ............ A61B 17/1671; A61B 17/7092; A61B 17/7074; A61B 17/7083; A61B 2090/062; G01B 3/28
USPC ......... 606/86 A, 102, 106; 600/587; 33/836, 33/512; 702/166
See application file for complete search history.

(56) References Cited

U.S. PATENT DOCUMENTS

| | | | | |
|---|---|---|---|---|
| 5,928,243 A | * | 7/1999 | Guyer | A61B 17/1671 606/102 |
| 2008/0154280 A1 | * | 6/2008 | Schumacher | A61B 17/708 606/104 |
| 2010/0137874 A1 | * | 6/2010 | Kim | G01B 3/28 606/102 |
| 2015/0305786 A1 | * | 10/2015 | Wehrle | A61B 90/98 606/86 A |

FOREIGN PATENT DOCUMENTS

DE    202005011355    11/2005

OTHER PUBLICATIONS

German Search Report for German Application No. 10 2015 101 650.8 mailed Sep. 8, 2015, including English translation.

* cited by examiner

*Primary Examiner* — Pedro Philogene
(74) *Attorney, Agent, or Firm* — RatnerPrestia

(57) ABSTRACT

A detection and indication device for the detection and indication of the presence or absence of a stabilization bar in the tulip head of a pedicle screw includes a housing. The housing is adjusted in such a way that it can be connected with elongated flanks of the pedicle screw or a downtube coupled to the pedicle screw in a detachable manner. A detection bar can be mounted axially movable in the housing. The relative positioning of the detection bar to the housing indicates a detection result. A system for spinal stabilization includes at least one pedicle screw with a tulip head and elongated flanks or a downtube coupled to the pedicle screw, at least one stabilization bar and a detection and display device.

10 Claims, 3 Drawing Sheets

US 9,622,797 B2

1

Figure 1:
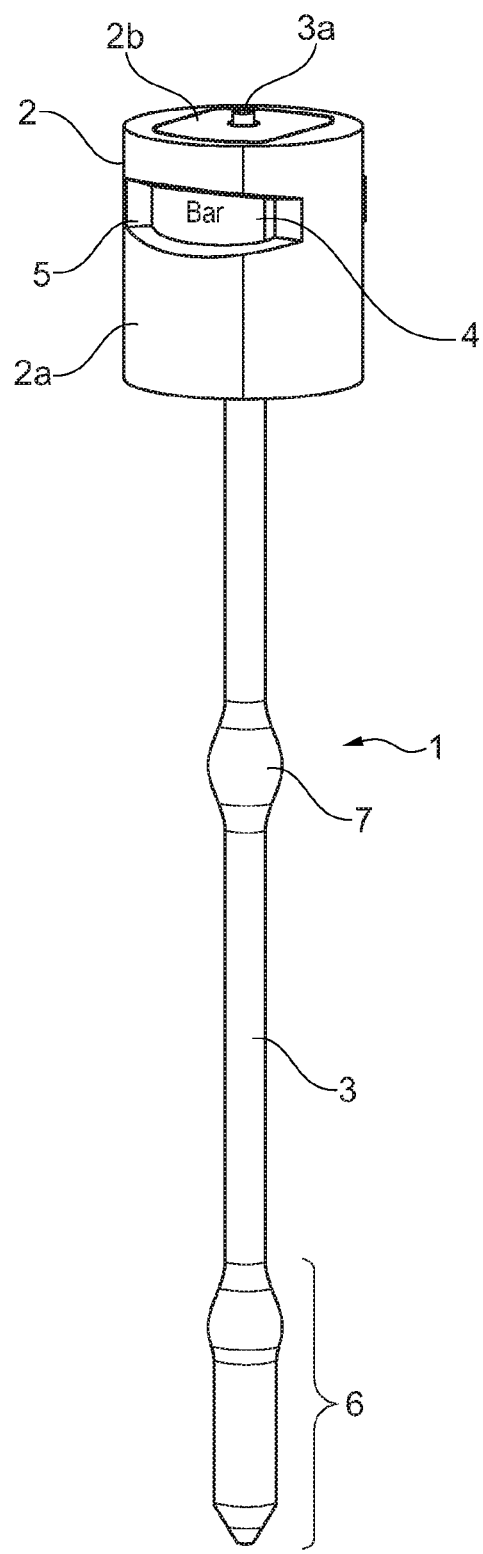

DETECTION AND DISPLAY DEVICE FOR PEDICLE SCREW AND SPINAL STABILIZATION SYSTEM WITH DETECTION AND DISPLAY DEVICE

RELATED APPLICATION(S)

This application is related to and claims the benefit of priority of German Application No. DE 10 2015 101 650.8, filed Feb. 5, 2015, the contents of which is incorporated by reference herein for all purposes.

FIELD

The present invention relates generally to spinal stabilization systems, and in particular to a detection and indication/display device for the detection and indication/display of the presence or absence of a stabilization bar in the tulip head of a pedicle screw, and further to a spinal stabilization system with at least one pedicle screw, at least one stabilization bar and at least one such detection and display device.

BACKGROUND

During percutaneous surgery on the spinal column, in particular percutaneous spinal stabilization surgeries, several pedicle screws are screwed in several vertebral bodies in most cases, and then the pedicle screws are connected with each other by means of a connecting or stabilization bar in such a way that the stabilization rod fixes the vertebral bodies in a desired position in relation to each other.

In most cases, the pedicle screws used for such a vertebral reposition have a screw head in the shape of a tulip, a so-called tulip head. Furthermore, the pedicle screws have in most cases elongated flanks which extend from the tulip head in the longitudinal direction of the pedicle screw and block off the instrument access to the tulip head from the surrounding tissue. After the successful placement of the implant, the elongated flanks are removed from the pedicle screws.

As an alternative to pedicle screws with elongated flanks, pedicle screws with flanks of a regular length in combination with pipe-shaped attachments, so-called downtubes, can be used as well. Here, one downtube each is placed on the tulip head of one pedicle screw each and/or is connected with the pedicle screw/coupled with it in a detachable manner and also serves to block off the instrument access to the tulip head from the surrounding tissue.

After the pedicle screws have been screwed in the respective vertebral bodies, the stabilization bar is threaded through entrance openings between the elongated flanks and/or in the downtube of each pedicle screw in the tulip head of each of the pedicle screws, with the downtube connected and/or with elongated flanks connected with the pedicle screw.

After the stabilization bar has been threaded in and placed in the tulip heads of all desired pedicle screws, the stabilization bar is fixed in each pedicle screw by means of a set screw. The set screw is screwed in each tulip head of each pedicle screw through the instrument access kept open by the elongated flanks and/or the downtube.

In practice, the threading in of the stabilization bar in the tulip heads of the pedicle screws is extremely difficult because the operating physician/surgeon cannot see the entrance openings between the elongated flanks and/or the entrance openings in the downtube of a respective pedicle screw. As a result, the operating physician/surgeon has to

2 blindly guess where the entrance opening of each pedicle screw is from the entrance opening of the stabilization bar in the body and try to hit it. It is particularly challenging to thread in the stabilization bar when the stabilization bar is relatively long and/or when relatively many pedicle screws have to be connected with each other. This is aggravated by the fact that the pedicle screws often are offset relative to each other because of different screw-in angles and are therefore not aligned with each other.

For this reason, the operating physician/surgeon tries in most cases to deduce the position of the distal end of the stabilization bar from his point of view from the position and alignment of the bar insertion device used to move and introduce the stabilization bar. Here, the bar insertion device is an instrument with which the operating physician/surgeon grasps and moves the stabilization bar during the threading-in process.

First, the operating physician/surgeon introduces the stabilization bar in the patient's body and tries to navigate it towards a first pedicle screw. When the downtube of the pedicle screw and/or the elongated flanks of it start(s) to move, this movement indicates to the operating physician/surgeon that the distal end of the stabilization bar is close to the pedicle screw and/or rests on it. As soon as the downtube and/or the elongated flanks start(s) to move, the operating physician/surgeon tries to thread in and/or slide in the stabilization bar. Due to the above-mentioned offset between the pedicle screws, however, the stabilization bar may also be slid past the downtube and/or the elongated flanks of the pedicle screw on the outside.

A check of the correct positioning of the stabilization bar during or also after surgery by means of radiography is not possible because with radiographs taken in the anterior-posterior direction, the downtubes and/or the screw heads of the pedicle screws block the beam path. Even with radiographs taken in the lateral direction, the position of the stabilization bar can be determined only insufficiently because the position of the stabilization bar can be detected, but not whether it is also in the right spatial depth, i.e. in or next to the downtube and/or between or next to the elongated flanks of each pedicle screw. So the operating physician/surgeon gets no feedback and so is not able to check either whether the stabilization bar is in the downtube and/or between the elongated flanks of a selected pedicle screw.

In practice, the operating physician/surgeon tries to make do in most cases with introducing a screwdriver shaft in the instrument access defined by the downtube and/or the elongated flanks of a pedicle screw and then jiggles the bar insertion device connected with the stabilization bar. When the screwdriver shaft moves, this indicates the stabilization bar is in the downtube and/or between the elongated flanks. However, this procedure only allows for a very imprecise and relatively error-prone registration of the presence or absence of the stabilization bar in the tulip head of the pedicle screw.

Another possible solution would be to equip the tulip head of the pedicle screw and/or the end of the downtube facing the pedicle screw with a lamp which enables the operating physician/surgeon to perform a direct visual check of the positioning of the stabilization bar, but the costs of a such a system would not be acceptable from a financial point of view.

In summary, it has to be noted therefore that the insertion of the stabilization bar in the tulip heads of the pedicle screws is usually accomplished based on the trial-and-error method. This very imprecise and time-consuming procedure increases the stress on the patient caused by the surgery because of extended anaesthesia times as well as the price of the surgery.

SUMMARY

The task of the invention in hand is the creation of a detection and indication/display device for detecting and clearly indicating the presence or absence of a stabilization bar in the tulip head of a pedicle screw, which enables the operating physician/surgeon to find out in a clear, error-free and reproducible manner at any time during surgery whether a stabilization bar has been introduced in the tulip head of a certain pedicle screw or not.

This task is solved by the detection and indication device and the system for spinal stabilization as described herein.

In the following, the detection and indication device will also be referred to as a detection and display device. A detection and display device according to the invention has a housing which is adapted in such a way that it can be connected with the elongated flanks and/or the downtube of a pedicle screw in a detachable manner, and a detection bar mounted axially movable in the housing, the relative positioning of which to the housing indicates a detection result.

The invention is based on the realisation that the threading in of the stabilization bar in the tulip head of the pedicle screw and/or the subsequent screwing in of a set screw reduces the axial length of the instrument access defined by the elongated flanks and/or the downtube of the pedicle screw. For this reason, the axial length of the instrument access defined by the elongated flanks and/or the downtube of the pedicle screw indicates the presence or absence of the stabilization bar and/or the set screw in the tulip head of the pedicle screw.

Now the basic principle of the invention is to take advantage of this connection between the changes of the axial length of the instrument access duct and the presence or absence of the stabilization bar and/or the set screw in the tulip head of the pedicle screw in order to verify the correct positioning of the stabilization bar and/or the set screw in the pedicle screw. Here, first the housing of a detection and display device according to the invention is connected with the elongated flanks and/or a downtube of the pedicle screw in a detachable manner. For example, the housing is fit, placed or also screwed on the flanks and/or the downtube. Depending on the axial length of the instrument access duct, then the detection bar axially movable in the housing of the detection and display device according to the invention can be introduced in the instrument access more deeply or less deeply. The end of the detection bar facing the pedicle screw is preferably designed in such a way that the detection bar can get out of the way along the longitudinal direction of the elongated flanks and/or the downtube when the stabilization bar is introduced in the instrument access.

The resulting relative positioning between the housing of the detection and display device according to the invention connected with the elongated flanks and/or the downtube of the pedicle screw in a detachable manner and the detection bar therefore reflects the axial length of the instrument access duct and consequently indicates the presence or absence of the stabilization bar and/or the set screw in the tulip head of the pedicle screw.

According to a possibly separately claimable claim of the invention in hand, the housing basically has the shape of a cylindrical sleeve, and the detection bar has at least one mark which clearly indicates a predetermined relative positioning of the detection bar to the housing. In the easiest case, this is a mark written on the detection bar or cut in the detection bar, which is arranged on the detection bar in such a way that it is only visible in the presence or absence of the stabilization bar, therefore when the instrument access is shortened as compared to a case of absence of the stabilization bar in the tulip head of the pedicle screw, and therefore the detection bar cannot be introduced in the instrument access that deeply and keeps protruding from the instrument access. In addition, the detection bar can have several marks along its axial length arranged like a scale which indicate the relative positioning of the detection bar to the housing.

As an alternative and/or in addition to marks written on or applied to the detection bar, marks in the shape of a different surface structure (e.g. roughened spots, etc.) are also conceivable. Also the detection bar as well as the housing can have a mark, which are brought into contact with each other in case of a predetermined relative positioning of the detection bar to the housing, after which a suitable, for example acoustic, signal is output.

According to another, possibly separately claimable aspect of the invention, the housing has a recess by means of which the at least one mark of the detection bar from outside the display device can be read off, for example visually or tactilely. Such a furnishing of the housing with a recess makes it possible to make the detection and display device according to the invention more compact on the whole because it is not necessary for the detection bar to protrude from the housing at its end on the housing side for reading off of the detection result. In addition, the end of the detection bar on the housing side is protected by the housing so that any damage to the detection and display device during transportation and use can be reduced, which increases the useful life of the detection and display device.

According to another, possibly separately claimable aspect of the invention in hand, the housing has a first housing part and a second housing part that is mounted in the second housing part in an axially movable manner. In this embodiment, the first housing part is preferably adapted in such a way so that it can be connected with the elongated flanks and/or the downtube of the pedicle screw in a detachable manner, for example by means of fitting or screwing the first housing part on the elongated flanks and/or the downtube. Preferably, a relative positioning between the second housing part and the first housing part indicates a detection result. Advantageously, the first and second housing parts are basically provided as two sleeves concentrically arranged to each other here.

According to another, possibly separately claimable aspect of the invention, the second housing part is fixed in the detection bar in such a way that a movement of the detection bar results in a corresponding movement of the second housing part. Preferably the second housing part is directly connected with the detection bar here. For example, the detection bar can be glued in the second housing part or the second housing part and the detection bar can be provided as a unit made of a single piece of material.

Here, it is furthermore advantageous that the second housing part has at least one mark which clearly indicates a predetermined relative positioning of the detection bar and so of the second housing part to the first housing part. Similarly to the marks added directly on the detection bar, the at least one mark on the second housing part can also be a mark, for example in the shape of a drawing, an indentation or a changed surface. For example, the second housing part can have more than two marks in different positions along its axial direction, such as the marks "No bar", "Bar"

and "Set screw". Depending on the relative positioning of the second housing part to the first housing part, a suitable predetermined mark is displayed. The detection bar as well as the second housing part can also have a mark each which are brought in contact with each other at a predetermined relative positioning of the detection bar to the second housing part, after which a suitable, for example acoustic, signal is output.

Advantageously, the first housing part has, with this design of the invention, a recess with which the at least one mark of the second housing part can be read off from outside the detection and display device.

According to another, possibly separately claimable aspect of the invention, the detection bar cannot only be moved axially in the housing, but can also be swivelled around a defined predetermined swivel point arranged along the axial axis of the detection bar. This swivellable arrangement of the detection bar in the housing of the detection and display device according to the invention has the advantage that the presence of the stabilization bar cannot be displayed only as soon as the stabilization bar is in the tulip head, but that the operating physician/surgeon gets feedback as early as when he has arrived at the inlet of the entrance opening of the pedicle screw with the stabilization bar. That is to say, as soon as the stabilization bar touches the detection bar introduced in the instrument access between the elongated flanks and/or the downtube of the pedicle screw (however, before the detection bar starts moving axially), the detection bar is swivelled around the predetermined swivel point because the stabilization bar pushes on the end of the detection bar on the screw side in the introduction direction of the stabilization bar. In the style of a rocker, the pressure of the stabilization bar on the end of the detection bar on the screw side also swivels the end of the detection bar on the housing side.

Preferably, the detection bar has, according to another, possibly separately claimable aspect, at its end on the housing side, a preferably pin-shaped extension which (axially) protrudes from the boundary of the housing. This protrusion is firmly connected with the detection bar so that a swivelling of the detection bar results in a corresponding swivelling of the protrusion. As the protrusion protrudes from the boundary of the housing, the operating physician/surgeon can see the rotation of the protrusion and so knows that he has successfully navigated the stabilization bar to the entrance opening in the tulip head of the pedicle screw. Then the operating physician/surgeon can slide the stabilization bar in the tulip head of the pedicle screw.

According to another, possibly separately claimable aspect, the detection bar has, at the predetermined swivel point arranged along the axial axis of the detection bar, a preferably ball-shaped thickening which is integrated in a suitable recess in the housing and/or the second housing part in the style of a ball joint. Furthermore, the dimensions of the cross-section of a preferably cylindrical hollow space, in which the detection bar is guided in the housing, are preferably dimensioned in such a way that the cylindrical hollow space provides enough clearance for the pivoting of the detection bar.

A detection and display device according to the invention can be used during surgery for ongoing checking of the correct threading in of the stabilization bar in different pedicle screws as well as subsequent post-operative checking of the correct placement of the stabilization bar.

Another and possibly also separately claimable aspect of the invention concerns a system for spinal stabilization with at least one pedicle screws with a tulip head and elongated flanks or a downtube coupled to the pedicle screw, at least one stabilization bar and at least one detection and display device according to the invention as described above.

BRIEF DESCRIPTION OF THE DRAWING FIGURES

Figure 2:
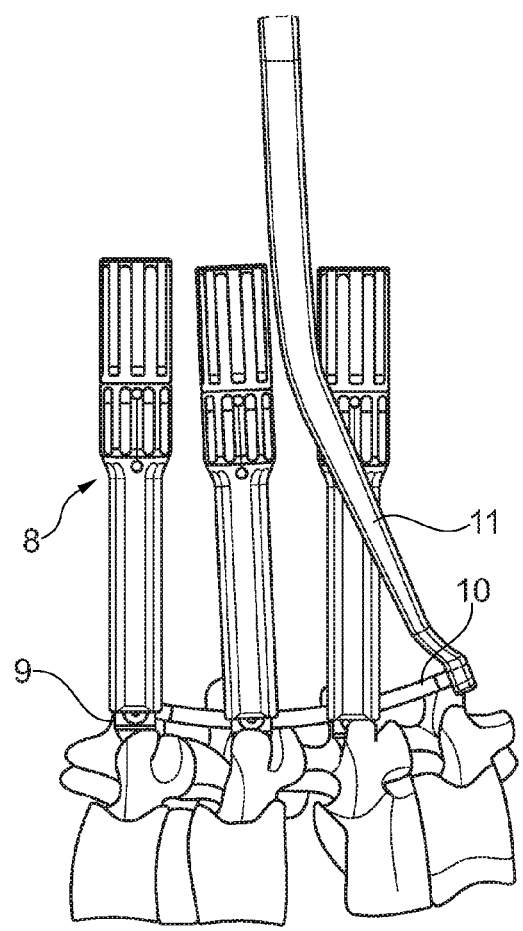
Figure 2A:
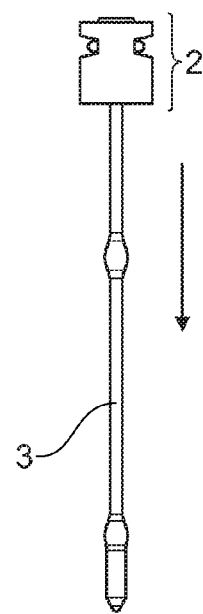
Figure 2B:
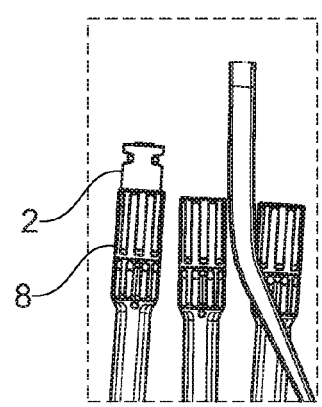
Figure 3A:
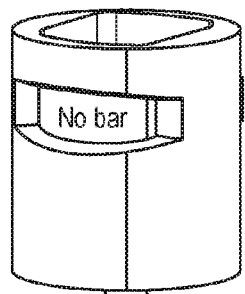
Figure 3B:
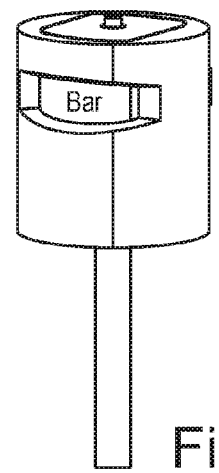
Figure 3C:
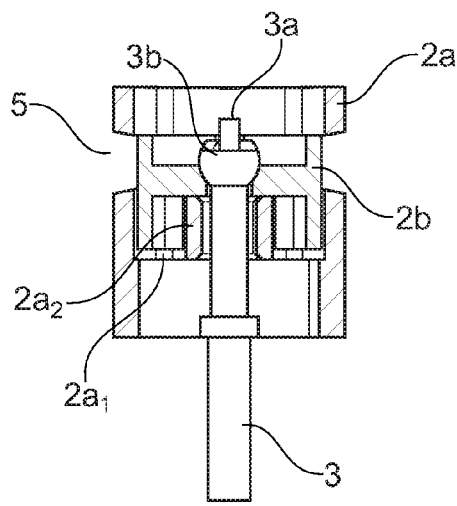
Figure 3D:
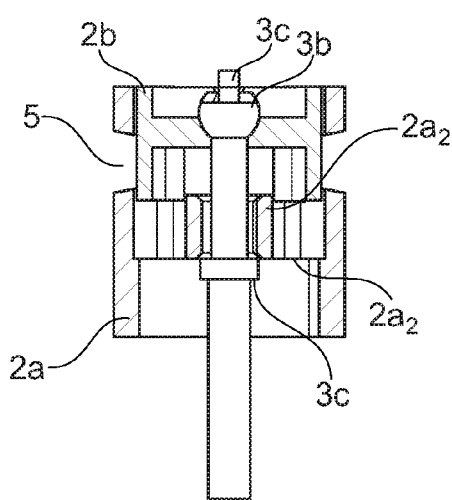
Figure 4:
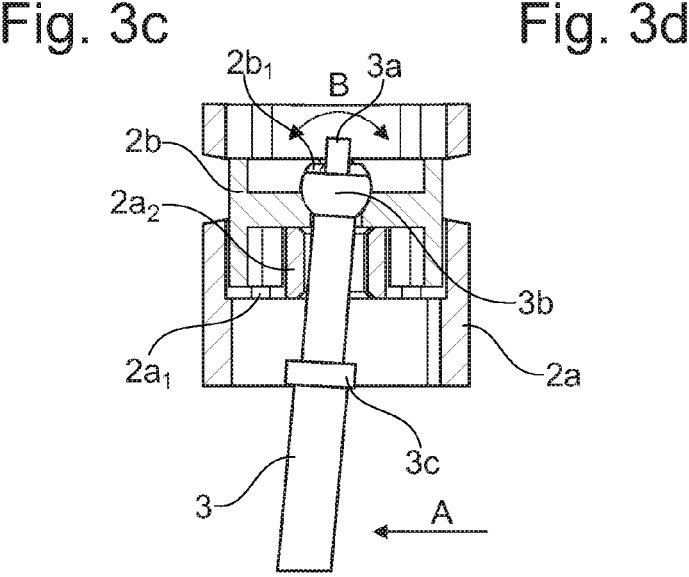

Further characteristics and advantages follow from the description below with regard to the respective figures. In the figures, the same reference signs refer to the same or very similar components. Here:

FIG. 1 shows a detection and display device according to the invention for the detection and display of the presence or absence of a stabilization bar in the tulip head of a pedicle screw, FIGS. 2 and 2*a* show the introduction of the detection bar of the detection and display device from FIG. 1 in a downtube of a pedicle screw during percutaneous surgery, FIG. 2*b* shows a detailed view of a downtube with the housing of the detection and display device placed on the downtube from FIG. 1, FIG. 3*a* shows an outside view of the housing of the detection and display device from FIG. 1 in the position that indicates the absence of a stabilization bar, FIG. 3*b* shows an outside view of the housing of the detection and display device from FIG. 1 in the position indicating the presence of a stabilization bar, FIG. 3*c* shows a cross-sectional view of the housing of the detection and display device from FIG. 1 in the position indicating the absence of a stabilization bar, FIG. 3*d* shows a cross-sectional view of the housing of the detection and display device from FIG. 1 in the position indicating the presence of a stabilization bar, and FIG. 4 shows an embodiment of a detection and display device according to the invention in which the detection bar is mounted in the housing not only axially movable, but also so that it can swivel.

DETAILED DESCRIPTION

FIG. 1 shows a detection and display device 1 according to the invention for the detection and display of the presence or absence of a stabilization bar in the tulip head of a pedicle screw with a housing 2, which is adjusted in such a way that it can be connected with elongated flanks of the pedicle screw or a downtube coupled with the pedicle screw in a detachable manner and a detection bar 3 mounted axially movable in the housing 2, the relative positioning of which to the housing 2 indicates a detection result. The housing has a first housing part 2*a* and a second housing part 2*b* mounted axially movable in the first housing part 2*a*. The first and second housing parts (2*a*,2*b*) are basically provided in the shape of two sleeves arranged concentrically to each other. The second housing part 2*b* is fixed on an axial end of the detection bar 3 in such a way that a movement of the detection bar 3 in the axial direction causes a corresponding movement of the second housing part 2*b*. On its end facing away from the detection bar 3, the basically sleeve-shaped second housing part 2*b* is closed so that it forms the cover of the housing 2. The detection bar 3 has a pin-shaped axial protrusion 3*a* which protrudes from the boundary of the second housing part 2*b* that forms the cover of the housing 2. In this embodiment, the second housing part 2*b* has two axially spaced marks 4, which clearly indicate a predetermined axial relative positioning of the detection bar 3 and so of the second housing part 2*b* to the first housing part 1. In addition, the housing part 2*a* has a window-like recess 5 on the circumference side, through which one mark 4 each of the second housing part 2a can be read off from outside the detection and display device 1. Depending on the relative positioning of the detection bar 3 and consequently the second housing part 2b to the first housing part 1, a predetermined mark 4 is visible through the recess 5. In FIG. 1, the detection bar 3 and consequently the housing part 2b are in a relative positioning to the first housing part 2a which is assigned to the presence of the stabilization bar 10 in the tulip head of the pedicle screw 9. For this reason, the display and/or mark 4 "Bar" assigned to the presence of the stabilization bar 10 is visible through the recess 5 in the view shown in FIG. 1.

On its end facing away from the housing 2, i.e. the screw-side (distal) end, the detection bar 3 is designed in such a way that it moves out of the way in the axial direction to the housing 2 when a stabilization bar 10 is threaded in the tulip head of the pedicle screw 9. For this purpose, the screw-side end area of the detection bar 3 has a thickening 6 the dimensions of which are adjusted to the cross-section of the instrument access of the pedicle screw 9. In addition, the detection bar 3 has, along its axial length between the second housing part 2b and the distal thickening 6, another thickening or bead 7.

FIGS. 2 and 2a show the introduction of the detection bar 3 of the detection and display device 1 from FIG. 1 in a downtube 8 of a pedicle screw 9 during percutaneous surgery. Three pedicle screws 9 with one coupled downtube 8 each are screwed in one vertebral body each, as shown in FIG. 2. A stabilization bar 10 was already successfully threaded in the tulip heads of two pedicle screws 9. At one of its ends, the stabilization bar 10 is connected with a bar insertion device 11, by means of which the operating physician/surgeon moves the stabilization bar 10, like it is also known from the state of the art. The detection bar 3 is introduced into a downtube 8 in the direction as indicated by the arrow in FIG. 2a.

FIG. 2b shows a detailed view of a downtube 8 with the housing 2 of the detection and display device placed on the downtube 8 from FIG. 1 after the detection bar 3 was introduced in the downtube 8. Here, the sleeve-shaped first housing part 2b rests on the top edge of the downtube 8.

FIG. 3a is an external view of the housing 2 of the detection and display device 1 from FIG. 1 in the position that indicated the absence of a stabilization bar 10. When the housing 2 of the detection and display device 1 is placed on a downtube 8, the detection bar 3 moves maximally downwards (distally) in the downtube 8, i.e. in the direction to the pedicle screw 9. As a result of that, the second housing part 2b also moves maximally in the first housing part 2a in the direction to the pedicle screw 9, whereby the mark 4 "No bar" is moved into a position in which the mark 4 "No bar" of the second housing part 2b becomes visible through the recess 5 of the first housing part 2a. This shows the operating physician/surgeon that the stabilization bar 10 is not in the downtube 8/tulip head.

FIG. 3b shows an external view of the housing 2 of the detection and display device 1 from FIG. 1 in the position indicating the presence of a stabilization bar 10, in which the length by which the detection bar 3 can move in the downtube 8 in the direction to the pedicle screw 9 is shortened due to the presence of the stabilization bar 10 in the downtube 8. In other words, the detection bar 3 cannot be wholly introduced in the tulip head of the pedicle screw 9 because the stabilization bar 10 is in the downtube 8, but it rests on the stabilization bar 10. As a result, the second housing part 2b moves in the first housing part 2a in the direction away from the pedicle screw 9, whereby the mark 4 "Bar" is moved into a position in which the mark 4 "Bar" of the second housing part 2b becomes visible through the recess 5 of the first housing part 2a. This shows the operating physician/surgeon that the stabilization bar 10 is in the downtube 8.

FIG. 3c shows a cross-sectional view of the housing 2 of the detection and display device 1 from FIG. 1 in the position from FIG. 3a that indicates the absence of a stabilization bar 10. In this position, the second housing part 2b is maximally moved relative to the first housing part 2a in the direction to the pedicle screw 9. The axial movement of the second housing part 2b relative to the first housing part 2a in the direction towards the pedicle screw 9 is limited by a contact face $2a_1$ and/or a protrusion or collar $2a_1$, which are/is provided on the inside of the sleeve-shaped first housing part 2a running around the circumference, and on which the second housing part 2b rests in this relative positioning of the second housing part 2b to the first housing part 2a. On the radially inside edge of the protrusion $2a_1$, an inner guide sleeve $2a_2$ is provided, in which the detection bar 3 is guided and/or mounted. On its proximal end section, the detection bar 3 has a swivel point in the form of a ball-shaped thickening 3b which is integrated in a suitable recess of the second housing part 2b in the style of a ball joint. To be more specific, the sleeve-shaped second housing part 2b also has an inner all-round collar with central axial through-hole on which the ball-shaped thickening 3b is clamped or engaged axially and swivellable. In order to enable a swivelling of the detection bar 3 around the swivel point, the cross-section of the inner guide sleeve $2a_2$ is provided in such a way that there is an adjustment clearance between the detection bar 3 and the inner guide sleeve $2a_2$, i.e. a radial gap remains between the detection bar 3 and the inner guide sleeve $2a_2$.

FIG. 3d shows a cross-sectional view of the housing 2 of the detection and display device 1 from FIG. 1 in the position from FIG. 3b that indicates the presence of a stabilization bar 10. In this position, the second housing part 2b is maximally moved in the first housing part 2a in the direction away from the pedicle screw 9. The axial movement of the second housing part 2b relative to the first housing part 2a in the direction away from the pedicle screw 9 is limited by means of a limiting flange 3c, i.e. a protrusion that runs around the detection bar 3 in the form of a ring in the circumferential direction. The limiting flange 3c is firmly connected with the detection bar 3. As an alternative to a protrusion that runs around the detection bar 3 in the form of a ring in the circumferential direction, at least one knob or another, differently shaped protrusion can also be fitted to the detection bar 3, for example. In addition, a locally delineated roughening of the surface of the detection bar 3 or another surface treatment could also limit the axial movement of the detection bar 3.

FIG. 4 shows an embodiment of the detection and display device 1 according to the invention, in which the detection bar 3 is not only mounted axially movable, but also mounted swivellable in the housing 2, in a position in which the detection bar 3 is axially swivelled relative to the housing 2. If, for example, the detection bar 3 of the detection and display device 1 has been introduced in a downtube 8 and a stabilization bar 10 is introduced in the tulip head of the respective pedicle screw 9, the stabilization bar 10 first applies pressure on the detection bar 3 in the introduction direction A of the stabilization bar 10 before the stabilization bar 10 is introduced further in the tulip head of the pedicle screw 9 and the detection bar 3 moves out of the way in the direction away from the pedicle screw 9 and ends up resting on the stabilization bar 10. When the stabilization bar 10 applies pressure to the detection bar 3, the detection bar 3 mounted swivellable in the second housing part 2b is swivelled relative to the housing 2 in the introduction direction A. The swivelling movement of the detection bar along the arrow B occurs around the swivel point in the thickening 3b of the detection bar 3 which is integrated in the second housing part 2b in the style of a ball of a ball joint, and the swivelling movement is here limited by the wall of the inner guide sleeve $2a_1$. As a result of the swivelling of the detection bar 3, the pin-shaped protrusion 3a on the end of the detection bar 3 facing away from the pedicle screw 9 moves. In order to enable such a swivelling of the protrusion 3a, the cross-section of the opening $2b_1$ in the second housing part through which the protrusion 3a protrudes from the boundary of the second housing part 2b is provided in such a way that there is enough clearance between the protrusion 3a and the second housing part 2b so that the protrusion 3a can be swivelled. The movement of the protrusion 3a shows the operating physician/surgeon that the stabilization bar 10 touches the detection bar 10 and is therefore located at the entrance opening to the tulip head of the pedicle screw 9. This feedback tells the operating physician/surgeon that the stabilization bar 10 is in the right axis and he can insert the stabilization bar 10 in the tulip head of the pedicle screw 9.

The invention claimed is:

1. A detection and indication device for the detection and indication of the presence or absence of a stabilization bar in the tulip head of a pedicle screw the detection and indication device comprising:
    a housing which is adapted in such a way that it can be connected with elongated flanks of the pedicle screw or a downtube coupled with the pedicle screw in a detachable manner, and
    a detection bar that is mounted axially movable in the housing, the relative positioning of which to the housing indicates a detection result.

2. The detection and indication device according to claim 1, wherein the detection bar has at least one mark which clearly indicates a predetermined relative positioning of the detection bar to the housing.

3. The detection and indication device according to claim 2, wherein the housing has a recess through which the at least one mark of the detection bar can be read off from outside the detection and indication device.

4. The detection and indication device according to claim 1, wherein the housing has a first housing part and a second housing part mounted axially movable in the first housing part.

5. The detection and indication device according to claim 4, wherein the second housing part is mounted on the detection bar in such a way that a movement of the detection bar results in a corresponding movement of the second housing part.

6. The detection and indication device according to claim 4, wherein the second housing part has at least one mark which clearly indicates a predetermined relative positioning of the detection bar and the second housing part to the first housing part.

7. The detection and indication device according to claim 4, wherein the first housing part has a recess through which the at least one mark of the second housing part can be read off from outside the detection and indication device.

8. The detection and indication device according to claim 1, wherein the detection bar is not only mounted axially movable in the housing, but also mounted axially swivellable relative to the housing.

9. The detection and indication device according to claim 8, wherein the detection bar has, at its end on the housing side, a pin-shaped protrusion which protrudes from the boundary of the housing.

10. A system for spinal stabilization comprising at least one pedicle screw with a tulip head and elongated flanks or a downtube coupled to the pedicle screw, at least one stabilization bar and at least one detection and indication device according to claim 1.

\* \* \* \* \*